United States Patent
Lynch-Branzoi et al.

(10) Patent No.: US 12,324,685 B2
(45) Date of Patent: Jun. 10, 2025

(54) ELASTOMERS ENHANCED WITH IN SITU FORMATION OF 2D NANOPARTICLES FROM LAYERED MATERIALS FOR MULTIFUNCTIONAL SENSORS

(71) Applicant: Rutgers, The State University of New Jersey, New Brunswick, NJ (US)

(72) Inventors: Jennifer K. Lynch-Branzoi, Belle Mead, NJ (US); Ali Ashraf, Paterson, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 419 days.

(21) Appl. No.: 17/759,209

(22) PCT Filed: Jan. 28, 2021

(86) PCT No.: PCT/US2021/015357
§ 371 (c)(1),
(2) Date: Jul. 21, 2022

(87) PCT Pub. No.: WO2021/154903
PCT Pub. Date: Aug. 5, 2021

(65) Prior Publication Data
US 2023/0080867 A1 Mar. 16, 2023

Related U.S. Application Data

(60) Provisional application No. 62/966,711, filed on Jan. 28, 2020.

(51) Int. Cl.
*H01B 1/20* (2006.01)
*A61B 5/00* (2006.01)
(Continued)

(52) U.S. Cl.
CPC ............. *A61B 5/6833* (2013.01); *C08J 3/203* (2013.01); *C08K 3/042* (2017.05); *C08K 3/38* (2013.01);
(Continued)

(58) Field of Classification Search
CPC ..... A61B 5/6833; C08J 3/203; C08J 2383/04; C08J 3/20; C08K 3/042; C08K 3/38;
(Continued)

(56) References Cited

U.S. PATENT DOCUMENTS

2007/0158618 A1* 7/2007 Song ................... H01M 8/0223
252/500
2011/0015469 A1 1/2011 Walter et al.
(Continued)

FOREIGN PATENT DOCUMENTS

WO 2019182535 A2 9/2019

*Primary Examiner* — Mark Kopec
*Assistant Examiner* — Jaison P Thomas
(74) *Attorney, Agent, or Firm* — FOX ROTHSCHILD LLP (57) ABSTRACT

Disclosed is a concise, inexpensive and scalable method for preparing elastomers filled with conductive 2D nanoparticles. The method comprises independently filling elastomer polymer precursors and/or corresponding elastomer polymer curing agents or their precursors with conductive 2D nanoparticles by shear exfoliation of a layered material, followed by mixing the two components and curing to form the elastomer. Such filled elastomers have utility in preparing various types of sensors which are useful in a variety of practical applications and devices.

19 Claims, 5 Drawing Sheets

(51) Int. Cl.
*C08J 3/20* (2006.01)
*C08K 3/04* (2006.01)
*C08K 3/38* (2006.01)

(52) U.S. Cl.
CPC ............ *H01B 1/20* (2013.01); *C08J 2383/04* (2013.01); *C08K 2003/385* (2013.01); *C08K 2201/001* (2013.01); *C08K 2201/011* (2013.01); *C08K 2201/014* (2013.01)

(58) Field of Classification Search
CPC ........ C08K 2003/385; C08K 2201/001; C08K 2201/011; C08K 2201/014; H01B 1/20; H01B 1/22; H01B 1/24; B82Y 15/00; B82Y 40/00; C01B 32/194
See application file for complete search history.

(56) References Cited

U.S. PATENT DOCUMENTS

| | | | |
|---|---|---|---|
| 2015/0159030 A1* | 6/2015 | Decker | C08L 33/14 252/511 |
| 2015/0267030 A1* | 9/2015 | Nosker | C08K 3/04 524/496 |
| 2017/0369320 A1* | 12/2017 | Zhamu | C09D 11/52 |
| 2018/0155532 A1 | 6/2018 | Pan et al. | |
| 2019/0185672 A1* | 6/2019 | Boland | C08L 83/04 |
| 2019/0233611 A1 | 8/2019 | Nosker et al. | |
| 2021/0122900 A1* | 4/2021 | Pang | C08K 3/38 |
| 2021/0277193 A1* | 9/2021 | Gomez Cordon | C08J 3/203 |

\* cited by examiner

ELASTOMERS ENHANCED WITH IN SITU FORMATION OF 2D NANOPARTICLES FROM LAYERED MATERIALS FOR MULTIFUNCTIONAL SENSORS

CROSS-REFERENCE TO RELATED APPLICATIONS

This application claims priority under 35 U.S.C. § 119(e) to U.S. Provisional Patent Application Ser. No. 62/966,711, filed on Jan. 28, 2020, which is hereby incorporated by reference in its entirety.

FIELD OF THE INVENTION

The present invention relates to new methods of preparing elastomer composites containing fillers of conductive 2D layered nanoparticles. These methods are cost-effective and scalable, and constitute a commercializable entry into various sensors useful in medical devices, fitness monitors, and related wearable devices and items.

BACKGROUND

Elastomers and rubber-based composites containing conductive fillers provide several advantages compared to conventional rigid sensors. Conductive elastomeric polymer and rubber-based composites are capable of withstanding large strain in multiple directions, are biocompatible, lightweight, consume low power, can be stretchable, are flexible and therefore wearable. Due to these unique properties, such sensors are flexible and can be incorporated into clothing and garments or into barrier (protective) gloves (glove-based chemical sensors), and can even be directly applied to skin.

Among different conductive fillers, graphene (single, few and multi-layer) and exfoliated graphite are of great interest due to exceptional mechanical properties, thermal and electrical conductivities, stability and large surface area. This class of graphene-enhanced elastomeric composites, henceforth referred to as G-EMCs, depends on unique properties of both the graphene/graphite and the elastomer/rubber to sense its environment. Under external load, the distance between graphene particles in the composite and the structure of the hexagonal honeycomb will undergo change, resulting in a change in resistance of the composite sensor. When the filler content is above the percolation threshold in the composite, electrons tunnel or hop from one graphene flake to another; therefore, the change in distance between graphene flakes changes the resistance to electron flow.

In addition, these sensors show high sensitivity and minimal hysteresis, resulting in reproducible signals during repetitive movement of 1 Hz frequency. Besides strain sensors for human motion monitoring, G-EMCs can be used for tactile sensors for touch screen displays, for temperature sensing (since the electron tunneling effect is dependent on the temperature of the composite), and for pressure and flow sensing. Graphene natural rubber composite has been used for liquid solvent sensing, since exposure to solvent leads to swelling (i.e., change in the distance between fillers), which increases the resistance of the composite.

Over the last decade, many researchers have shown the multifunctionality of this type of sensor, with specific applications in fabrics, in articles such as gloves, in flexible electronics, in chemical monitoring, in health monitoring, and in temperature monitoring. However, conventional methods utilized to produce graphene are multi-step, expensive and have the potential to include impurities during preparation and transfer into the target polymer matrix. Moreover, mixing of defect-free and inert pristine graphene with elastomers and rubber is difficult, typically producing inhomogeneous mixtures which show agglomeration in the matrix. Therefore, elastomers and rubbers like polydimethylsiloxane (PDMS), ECOFLEX® and dragon-skin (platinum catalyzed silicone), and polyisoprene are usually mixed with functionalized nanofillers using several techniques, including melt processing, in-situ polymerization, and solution blending to fabricate G-EMCs. Specifically, solution-processed graphene electrodes are deemed impractical because of structural defects in the graphene formed by an oxidation/reduction process. See https://www.sigmaaldrich.com/technical-documents/articles/materials-science/graphene-based-transparent-conductive-electrodes.html.

Among these methods, melt processing shows the most potential for commercialization, but has certain limitations including poor dispersion and material degradation. All of these limitations hinder commercialization of G-EMC-based sensors.

With regard to the state of the art, graphene is known to be produced from graphite by ultrasonic tip sonication in N-methyl-pyrrolidone (NMP) for 72 hours, followed by centrifugation for 90 min, vacuum filtration through membrane, then dispersion in chloroform using ultrasonication for 1.5 hours. Other applicable mechanical graphite exfoliation techniques include ball milling, pressure driven fluid dynamics, jet cavitation, supercritical fluid treatment, and tube shear. Typically the prior art then produces a G-putty matrix by blending the graphene in putty for 2 hours, followed by sonication for 2 hours, heating on a hot plate for 6 hours, then drying for 12 hours, and finally heating for 45 min to produce the G-putty.

SUMMARY OF THE DISCLOSURE

Even though nanomaterials, particularly graphene-based sensors, have shown tremendous promise, their use is limited due to both high cost and the complexity of production. The presently disclosed method produces nanomaterial sensors in an inexpensive one-step process that is suitable for commercialization.

Provided herein are elastomers enhanced with 2D nanoparticles, whereby the nanoparticles are created by the application of shear to layered materials with subsequent exfoliation of the layers occurring directly within the elastomer precursor and/or curing agent precursor components, thereby producing the cured elastomer nanocomposites with beneficial electromechanical and thermal properties. Elastomers are thermoset polymers, which are highly viscoelastic in nature, that are formed by combining precursors, including the elastomer precursor and curing agent, to induce polymerization and curing. Elastomers are lightly cross-linked so that they are flexible and stretchy.

A suitable layered material (or combination of layered materials), such as graphite, hexagonal boron nitride (HBN), molybdenum disulfide ($MoS_2$), or tungsten disulfide ($WS_2$), is combined with the elastomeric precursor component in a batch mixer that imparts uniform, high shear to exfoliate the layers from the layered materials to provide 2D nanoparticles (having a distribution in the number layers). Separately the layered material is combined with the curing agent component in a batch mixer that imparts uniform, high shear to exfoliate the layers from the layered materials to provide 2D nanoparticles (with a distribution in the number layers). The high shear exfoliation methods and equipment useful therefore as disclosed in U.S. Pat. No. 9,896,565 are incorporated herein by reference. Thus, 2D nanoparticles are well-distributed within one or both of the precursor components. Subsequently, the filled precursors are mixed together and allowed to cure, resulting in an elastomer nanocomposite with 2D nanoparticles, which provide improved mechanical, electrical, and/or thermal properties.

These flexible, conductive elastomeric nanocomposites have various commercial applications, including sensors for detecting pulse, blood pressure, temperature, small movements or deflection as a strain sensor (i.e. finger wag), tactile sensor, and chemical sensing and biosensing. Other potential application areas include temperature sensors, for example for automotive seating with heating/cooling capability; quality detection sensors for solvent mixtures, contaminated water in oceans, lakes, rivers, etc. chemical plant applications, surface drones (autonomous marine vehicles); structural monitoring (i.e. during seismic activity where damping capability of the elastomer is important); smart bandages where the sensor would be able to monitor pressure changes in the wound area; and coatings (one example would be for pipe systems in order to detect leaks).

One aspect of the invention is directed to a method of preparing an elastomer filled with conductive 2D nanoparticles comprising: a) providing an elastomer polymer precursor, a corresponding elastomer polymer curing agent, and one or more layered materials, where at least one of the layered materials is conductive when exfoliated into 2D nanoparticles; b) (i) blending the elastomer polymer precursor and at least one layered material under shear sufficient to exfoliate the layered material in the elastomer polymer precursor until 2D nanoparticles are formed, to provide covalently linked 2D nanoparticle-filled polymer precursor, and/or (ii) blending the elastomer polymer curing agent and at least one layered material under shear sufficient to exfoliate the layered material in the elastomer polymer curing agent until 2D nanoparticles are formed, to provide covalently linked 2D nanoparticle-filled curing agent; and c) mixing under curing conditions to form an elastomer: i) the 2D nanoparticle-filled polymer precursor and the elastomer polymer curing agent, or ii) the elastomer polymer precursor and the 2D nanoparticle-filled curing agent, or iii) the 2D nanoparticle-filled polymer precursor and the 2D nanoparticle-filled curing agent.

The polymer precursor:curing agent ratio can be about 4:1 to about 6:1. Preferably, 2D nanoparticle-filled polymer precursor and elastomer polymer curing agent are mixed in step c) to form an elastomer. Alternatively, elastomer polymer precursor and 2D nanoparticle-filled curing agent are mixed in step c) to form an elastomer. Alternatively, 2D nanoparticle-filled polymer precursor and 2D nanoparticle-filled curing agent are mixed in step c) to form an elastomer.

The method can further comprise a step of curing the polymer product under vacuum. The curing time under vacuum can be from about 0.1 hour to about 10 hours.

The layered material can be selected from the group consisting of graphite, hexagonal boron nitride (HBN), molybdenum disulfide ($MoS_2$), tungsten disulfide ($WS_2$) and mixtures of two or more thereof. Preferably, the layered material is graphite.

The elastomer polymer can comprise a precursor selected from the group consisting of polybutadiene, butadiene copolymers, acrylonitrile copolymers (NBR), natural rubber, synthetic rubbers, polyesteramides, chloroprene rubbers, poly(styrene-butadiene) copolymers, polysiloxanes, polyisoprenes, polyurethanes, polychloroprenes, chlorinated polyethylenes, polyethylene glycols (polyethylene oxides), polyester/ether urethanes, polyurethanes, polyethylene, propylene, chlorosulphanated polyethylene, polyalkylene oxides, polyethylene oxides, fluorosilicones, highly saturated nitriles (HSN, HNBR), nitriles, polyacrylates, silicones, fluorinated ethylene propylene (FEP), perfluoroelastomers, copolymers of tetrafluoroethylene/propylene, carboxylated nitriles, fluoroelastomers, and mixtures thereof.

The curing agent is selected based on compatibility with the elastomeric precursor and the desired end use application.

The blending under shear can be provided by a batch mixer.

Another aspect of the invention is directed to an elastomer filled with 2D nanoparticles prepared by above method.

A further aspect of the invention is directed to a method of fabricating a sensor, comprising attaching or inserting an elastomer filled with 2D nanoparticles prepared by the above method to a suitable substrate. The substrate can be selected from the group consisting of fabrics, rubbers, plastics, metal wood, electronic components, gloves, wrist bands, shoe soles, and belts.

An additional aspect of the invention is directed to a method of fabricating a sensor, comprising forming an elastomer filled with 2D nanoparticles prepared by the above method, into an appropriate shape for direct application to the surface to be monitored, including the skin of a subject to be monitored.

Another aspect of the invention is directed to a sensor prepared by either of the above fabrication methods.

DETAILED DESCRIPTION

Definitions

Elastomers are lightly cross-linked polymers, amorphous, and with a glass transition temperature below room temperature, that can undergo large reversible deformation.

Examples of elastomers include polybutadiene, ethylene propylene rubber, natural rubber (polyisoprene), polyurethane elastomer, silicone rubber, styrene butadiene rubber etc. Elastomers can be (1) one-part systems, which require no mixing and cure by moisture in the air, (2) two-part systems, which cure by a polymerization reaction that occurs when a curing agent is added, or (3) B-Stage systems, which are partially cured when the elastomer precursor and curing agent are mixed, and require elevated temperature for some time period to fully cure (solidify) the system. The curing agent selected must by compatible with the selected elastomer precursor. The curing ratio of polymer precursor/curing agent is dependent upon the type of polymer precursor, the specific curing agent, the desired property enhancement, and end use application (especially important in biomedical applications). The curing process can be completed at room temperature for many elastomers, as well as at elevated temperature in order to shorten curing time required. The specific curing conditions must be optimized for each type of elastomer system and desired properties of the elastomeric material.

Elastomers can be classified into three broad groups: diene, non-diene, and thermoplastic elastomers. However, for this technology, only the first two categories of elastomer are useful. Diene elastomers are polymerized from monomers containing two sequential double bonds. Typical examples include polyisoprene, polybutadiene, and polychloroprene. Nondiene elastomers include, butyl rubber (polyisobutylene), polysiloxanes (silicone rubber), polyurethane (spandex), and fluoro-elastomers. Non-diene elastomers have no double bonds in the polymer structure, and thus, crosslinking requires other methods than vulcanization, such as addition of trifunctional monomers (condensation polymers), or addition of divinyl monomers (free radical polymerization), or ethyl bridge formation using platinum complex catalyst (addition polymerization), or copolymerization with small amounts of diene monomers like butadiene.

One example of silicone elastomer used for this technology is ECOFLEX® 00-30. ECOFLEX® rubbers are platinum-catalyzed silicones (two-part (A and B precursors) silicone cured by addition polymerization) that are versatile and easy to use. ECOFLEX® rubbers are prepared by mixing precursors A:B by weight or volume and curing at room temperature, with negligible shrinkage. Low viscosity ensures easy mixing and de-airing. Cured rubber is very soft, very strong and very "stretchy", which is defined as stretching many times its original size without tearing, with subsequent rebounding to its original form without distortion.

Examples of layered materials capable of being exfoliated into conductive 2D nanoparticles include, without limitation: graphite, hexagonal boron nitride (HBN), and transition metal dichalcogenides (TMDs) (e.g., $MoS_2$, $MoSe_2$, $MoTe_2$, $WSe_2$, $TaSe_2$, $NbSe_2$, $NiTe_2$). Chalcogenides generally refer to oxygen (O), sulfur (S), selenium (Se), tellurium (Te), polonium (Po), and ununhexium (Uuh). These elements all contain six valence electrons and form 2-ions. Such layered materials may also include, without limitation, metal halides (e.g., $MoCl_2$, $PbI_2$, $MgBr_2$), layered metal oxides (e.g., $MnO_2$, $MoO_3$, $LaNb_2O_7$), layered double hydroxides (LDHs) (e.g., $Mg_6Al_2(OH)_{16}$), layered silicates or clays (e.g., montmorillonite (MMT), micas, vermiculite, talc, kaolinite), III-VI layered semiconductor (e.g., GaSe), layered V-VIs (e.g., $Bi_2Te_3$, $Sb_2Se_3$), layered α and γ zirconium phosphates and phosphonates, layered double hydroxides (LDHs), ternary transition metal carbides and nitrides, metal trichalcogenides, and metal trihalides. In some embodiments, the layered materials may be selected from the group consisting of HBN, $MoS_2$, mica, and kaolinite.

The term "conductive" as used herein refers to electrical conductivity, thermal conductivity, or both. The conductive 2D nanoparticles of the invention are preferably both electrically and thermally conductive. It has also been observed that a combination of a conductive 2D nanoparticle and a non-conductive 2D nanoparticle can enhance electrical conductivity by providing a focused path for electron mobility.

In the present method, a layered material which is capable of forming conductive 2D nanoparticles is exfoliated directly within one (for one-part elastomer) or both of the precursors of the elastomer (in case of two-part elastomer), viz., the elastomer precursor and/or curing agent, to shear the layers into conductive 2D nanoparticles having various number of layers in the c-axis direction, directly within these precursors, using a batch mixer or extruder that imparts uniform and high shear. The exfoliation methods previously developed for distributing graphene particles in a molten thermoplastic polymer phase by the application of a succession of shear strain events to the molten polymer phase, as disclosed in U.S. Pat. No. 9,896,565, are applicable to the present method. The high shear exfoliation methods and equipment useful therefore as disclosed in U.S. Pat. No. 9,896,565 are incorporated herein by reference. After subsequent mixing and curing of the filled precursors, an elastomer nanocomposite with conductive 2D nanoparticle enhancement is produced, having improved mechanical, electrical, and thermal properties. These 2D nanoparticles are preferably conductive both electrically and thermally.

To make successful sensor material, a one-part or two-part elastomer, and layered bulk materials like graphite, hexagonal boron nitride, molybdenum disulfide, tungsten disulfide are required. Depending on the weight percentage of graphene and other layered material nanoflakes in the composite sensor material, bulk filler materials are added to elastomer precursor in a beaker for premixing by hand. Then the premixed precursor-filler complex is poured into proprietary Randcastle batch mixer with an axial fluted extensional mixing element that imparts uniform, high shear, that is rotating at 150 RPM. In 30 minutes, bulk layered materials are sheared to nanoflakes within the precursor under nitrogen blanket due to the high shear force imparted by the batch mixer. In general, the RPM, mixing time, and temperature can be varied to optimize conditions for specific materials used.

For two-part elastomer, a similar procedure was followed for curing agent precursor. Then both parts are mixed in about 4:1 to about 6:1 (polymer:curing agent) curing ratio, or other suitable ratio based on the elastomer type and graphene concentration, degassed under vacuum and left to cure for 4-6 hours. In general, the curing ratio must be optimized for the specific materials used and the desired resulting properties. Prepared sensor material can transduce external stimuli (mechanical deformation, chemical reaction, heat) to electrical output using metal wiring or through antenna for wireless transmission to a data collection and processing electronics unit that will process the sensor output for display in a computer or cell phone. The sensor material can be a coating on a substrate. Without limitation, suitable sensor substrates can be selected from the group consisting of fabrics, rubbers, plastics, metal wood, electronic components, gloves, wrist bands, shoe soles, and belts.

The elastomer can comprise a pre-polymer, such as a lower molecular weight oligomer, that is either self-polymerized or is co-polymerized with another reactant to form the elastomer itself. Preferably, the pre-polymer is a low molecular weight elastomeric oligomer selected from the group consisting of polybutadiene, butadiene copolymers, acrylonitrile copolymers, natural and synthetic rubber, polyesteramides, chloroprene rubbers, poly(styrene-butadiene) copolymers, polysiloxanes (such as polydimethylsiloxane (PDMS) (silicone oil)), polyisoprene, poly-urethanes, polychloroprene, chlorinated polyethylene, polyethylene glycols (polyethylene oxides), polyester/ether urethanes, polyethylene, propylene, chlorosulphanated polyethylene, polyalkylene oxides, fluorosilicones, highly saturated nitriles (HSN, HNBR), nitriles, poly-acrylates, silicone, fluorinated ethylene propylene (FEP), perfluoroelastomers (such as SIMRIZ®), copolymers of tetrafluoroethylene/propylene (such as AFLAS®), carboxylated nitriles, fluoroelastomers (such as a dipolymer of hexafluoropropylene and vinylidene fluoride, e.g. DuPont™ VITON®), and mixtures thereof.

Further, a combination of layered materials can be incorporated in one or both of the precursors in order to tune the conductive or insulating properties of the resulting sensor, again both electrically and thermally.

Thus, one aspect of the invention is directed to a method of preparing an elastomer filled with 2D nanoparticles comprising: a) providing an unfilled elastomer polymer precursor, a corresponding unfilled elastomer polymer curing agent, and one or more layered materials, where at least one of the layered materials is capable of being exfoliated into conductive 2D nanoparticles; b) blending the unfilled elastomer polymer precursor and at least one layered material under shear sufficient to exfoliate the layered material in the elastomer polymer precursor until 2D nanoparticles are formed, to provide 2D nanoparticle-filled polymer precursor; and c) mixing the 2D nanoparticle-filled polymer precursor and unfilled elastomer polymer curing agent in a suitable ratio based on the elastomer type and graphene concentration, under curing conditions to form an elastomer. The ratio can be about 4:1, or about 4.5:1, or about 5:1, or about 5.5:1, or about 6:1, or another suitable ratio based on the elastomer type and graphene concentration.

Another aspect of the invention is directed to a method of preparing an elastomer filled with 2D nanoparticles comprising: a) providing an unfilled elastomer polymer precursor, a corresponding unfilled elastomer polymer curing agent, and one or more layered materials, where at least one of the layered materials is capable of being exfoliated into conductive 2D nanoparticles; b) blending the unfilled elastomer polymer curing agent and at least one layered material under shear sufficient to exfoliate the layered material in the elastomer polymer curing agent until 2D nanoparticles are formed, to provide 2D nanoparticle-filled curing agent; and c) mixing, the unfilled elastomer polymer precursor and the 2D nanoparticle-filled curing agent in a suitable ratio based on the elastomer type and graphene concentration, under curing conditions to form an elastomer. The ratio can be about 4:1, or about 4.5:1, or about 5:1, or about 5.5:1, or about 6:1, or other suitable ratio based on the elastomer type and graphene concentration.

Another aspect of the invention is directed to a method of preparing an elastomer filled with 2D nanoparticles comprising: a) providing an unfilled elastomer polymer precursor, a corresponding unfilled elastomer polymer curing agent, and one or more layered materials, where at least one of the layered materials is capable of being exfoliated into conductive 2D nanoparticles; b) (i) blending the unfilled elastomer polymer precursor and at least one layered material under shear sufficient to exfoliate the layered material in the elastomer polymer precursor until 2D nanoparticles are formed, to provide 2D nanoparticle-filled polymer precursor, and (ii) blending the unfilled elastomer polymer curing agent and at least one layered material under shear sufficient to exfoliate the layered material in the elastomer polymer curing agent until 2D nanoparticles are formed, to provide 2D nanoparticle-filled curing agent; and c) mixing the 2D nanoparticle-filled polymer precursor and the 2D nanoparticle-filled curing agent in a suitable ratio based on the elastomer type and graphene concentration, under curing conditions to form an elastomer. The ratio can be about 4:1, or about 4.5:1, or about 5:1, or about 5.5:1, or about 6:1, or other suitable ratio based on the elastomer type and graphene concentration.

Each of these methods can further comprise a step of curing the polymer product under vacuum. The curing time under vacuum can be from about 0.1 hour to about 10 hours. The vacuum curing time can be about 0.1, or about 0.2, or about 0.3, or about 0.4, or about 0.5, or about 0.6, or about 0.7, or about 0.8, or about 0.9, or about 1, or about 2, or about 3, or about 4, or about 5, or about 6, or about 7, or about 8, or about 9, or about 10 hours. The vacuum curing can be accomplished at room temperature, or with heating.

The layered material of each of these methods can be selected from the group consisting of graphite, hexagonal boron nitride (HBN), molybdenum disulfide ($MoS_2$), tungsten disulfide ($WS_2$), $MoSe_2$, $MoTe_2$, $WSe_2$, $TaSe_2$, $NbSe_2$, $NiTe_2$, $MoCl_2$, $PbI_2$, $MgBr_2$, $MnO_2$, $MoO_3$, $LaNb_2O_7$, $Mg_6Al_2(OH)_{16}$, GaSe, $Bi_2Te_3$, $Sb_2Se_3$, $TiSe_2$, $VS_2$, $NbS_2$, $TaS_2$, $VSe_2$, $NbSe_2$, $TaSe_2$, $VTe_2$, $NbTe_2$, $TaTe_2$, $PdTe_2$, $PtTe_2$, montmorillonite (MMT), mica, vermiculite, talc, kaolinite, borophene, phosphorene and mixtures of two or more thereof. Preferably, the layered material is graphite. The graphite can further comprise hexagonal boron nitride (HBN), and/or molybdenum disulfide ($MoS_2$), and/or tungsten disulfide ($WS_2$). Alternatively, the layered material is hexagonal boron nitride (HBN). Alternatively, the layered material is molybdenum disulfide ($MoS_2$). Alternatively, the layered material is tungsten disulfide ($WS_2$).

The unfilled curing agent of each of these methods curing agent is selected based on compatibility with the elastomeric precursor and the desired end use application.

The blending under shear of each of these methods can be provided by a batch mixer or suitable extruder.

Another aspect of the invention is directed to an elastomer filled with 2D nanoparticles prepared by any of the above methods.

A further aspect of the invention is directed to a method of fabricating a sensor, comprising attaching or inserting an elastomer filled with 2D nanoparticles prepared by any of the above methods to a suitable substrate. The substrate can be selected from the group consisting of fabrics, rubbers, plastics, metal wood, electronic components, gloves, wrist bands, shoe soles, and belts.

Another aspect of the invention is directed to a method of fabricating a sensor, comprising molding or casting an elastomer filled with 2D nanoparticles prepared by any of the above methods. This casting can also comprise wires or electrical connectors placed in the elastomer which, after casting become electrodes. The sensor can be molded, cast or otherwise applied to the intended substrate. Alternatively, the sensor can be molded or cast without a substrate for direct application to the surface to be monitored.

Another further aspect of the invention is directed to a method of fabricating a sensor, comprising forming an elastomer filled with 2D nanoparticles by any of the above methods, forming into an appropriate shape, and curing. As noted above, this can be accomplished by molding or casting. This casting can also comprise wires or electrical connectors placed in the elastomer which, after casting become electrodes. The so-formed sensor can be naturally adhesive to skin or other surface to which it is to be applied. Alternatively, the so-formed sensor can be coated with an adhesive for attachment, such as a skin contact adhesive when the sensor is to be attached to the skin of a subject to be monitored. An opening may be provided in the adhesive coating, allowing direct contact of the sensor to the surface being monitored.

The above methods of fabricating a sensor can further comprise the step of attaching electrical leads, electrical connectors, or electrodes thereto.

Another aspect of the invention is directed to a sensor prepared by any of the above fabrication methods.

Yet another aspect of the invention is directed to a sensor comprising a) a cured, molded or cast elastomer filled with conductive 2D nanoparticles; b) electrical leads, electrical connectors, or electrodes attached thereto; and c) optionally, an adhesive coating. The adhesive can be, for example, a skin contact adhesive for attachment of the sensor to the skin of a subject to be monitored.

The inventive GNF-enhanced elastomers can be used to detect pressure, force, stretch, displacement, touch, temperature, humidity and chemicals. These properties are advantageous for the production of various types of sensors as well as health monitoring devices to detect pulse, blood pressure, breathing, temperature, and strain (motion or deflection). Commercial applications include medical sensors such as those that measure patient movement, medical and laboratory PPE, electronic sensors for heat and exposure, health monitoring devices for measuring posture, activity and vital signs, and biosensing devices for measuring frailty, balance and posture. Products incorporating the devices include medical devices, laboratory PPE, health and fitness devices, and various electronics.

EXAMPLES

Example 1. Graphene in a Silicone Polymer

Figure 1A:
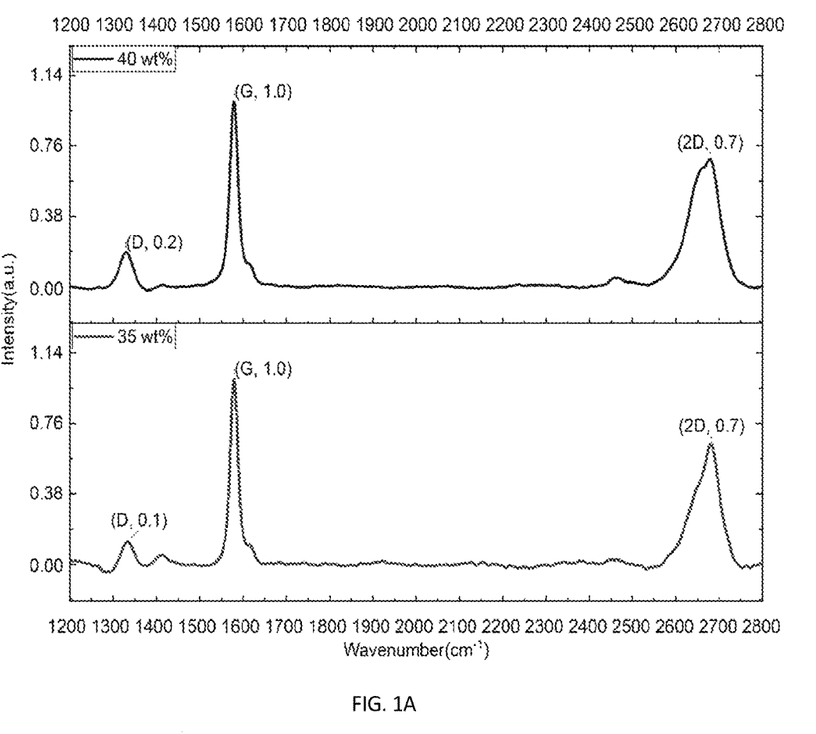
FIGS. 1A, 1B, 1C, 1D and 1E: 1A, Raman spectra of 35 and 40 wt % G-EMC sensor; 1B, 1C, 1D and 1E, SEM images of 40 wt % G-EMC sensor at different length scale.
Figure 1B:
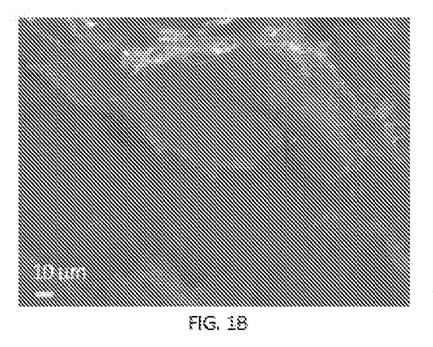
Figure 1C:
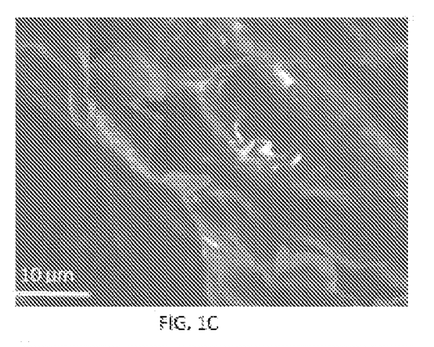
Figure 1D:
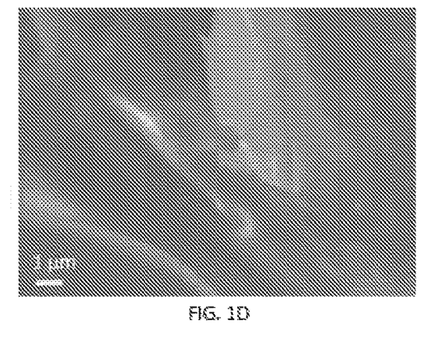
Figure 1E:
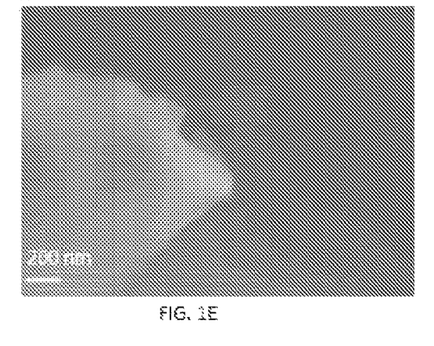
Figure 2A:
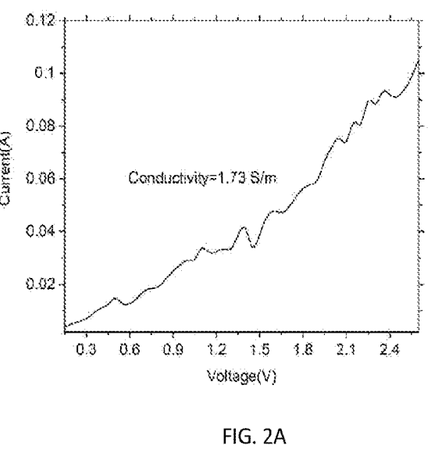
FIGS. 2A, 2B, 2C and 2D: 2A, I-V curve for 40 wt % G-EMC sensor; 2B, heart rate or pulse determination using G-EMC sensor; 2C, breathing detection using G-EMC sensor; 2D, speech detection using G-EMC sensor.
Figure 2B:
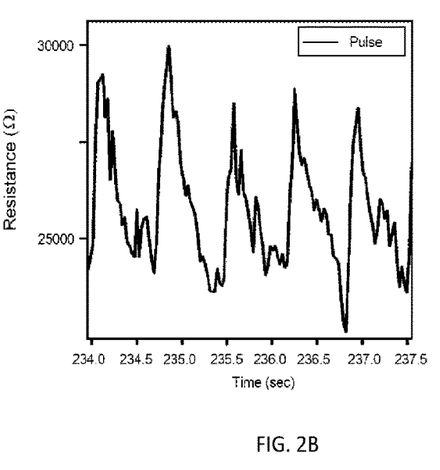
Figure 2C:
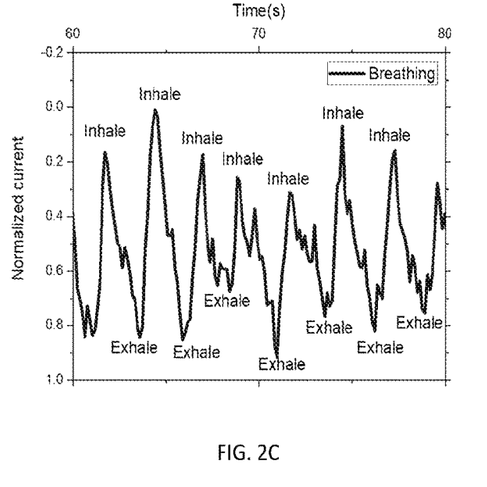
Figure 2D:
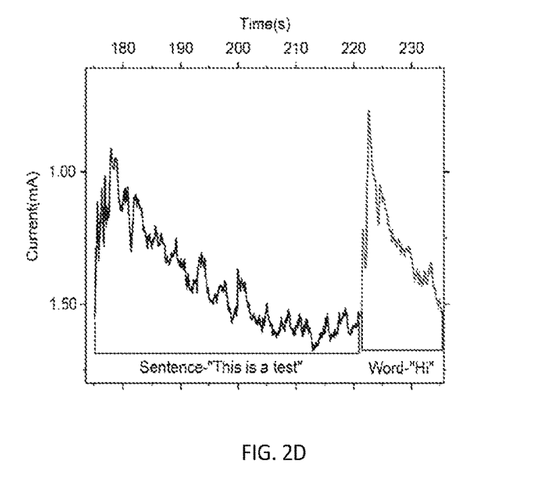

Using shear exfoliation, 35-40 wt % of graphite was converted into graphene nanoflakes (GNFs) directly within a silicone polymer precursor (ECOFLEX®/Dragon skin Part A) and the graphite was converted into GNFs directly within the curing agent (ECOFLEX®/Dragon skin Part B) component by mixing each sample in a batch mixer for 30-40 minutes at 40° C. temperature. With increasing mixing time, the degree of graphite exfoliation into GNFs increases and the distribution of the number of layers in the GNFs decreases. The GNF-matrix interaction is very strong, since each newly exfoliated GNF has a pristine surface, and fracturing across the AB Basal plane of the GNFs provides reactive sites with the potential for primary covalent bonding between GNF edges and the surrounding medium (either the polymer precursor or the curing agent) thereby providing in situ functionalization. The filled polymer precursor was then combined and mixed with the filled curing agent component and allowed to cure, according to the manufacturer's curing conditions but with a different mixing ratio (4-6 parts polymer precursor to 1 part of curing agent by weight). G-EMC sensors fabricated from polymers prepared in this fashion were tested for their applicability of health monitoring and temperature sensing. The G-EMC sensor was attached to the wrist for pulse detection (FIGS. 1A and 1B), near the nose for breathing detection (FIG. 2C) and on the throat for speech detection (FIG. 2D). Change in electrical current through the sensor was detected by a source measure unit (Keithley 2450) due to external stimuli coming from blood pressure in pulse, air flow during breathing, and vibration during speech. In all scenarios, a strong change in current was detected indicating good sensor performance. The applied voltage never exceeded 10 V, and therefore the power requirement is low for this class of sensors. Small artefacts in the signal coming from external noise can be eliminated by 1) hardware modification to minimize noise, and/or 2) appropriate mathematical interpolation and filtering algorithms.

Figure 3A:
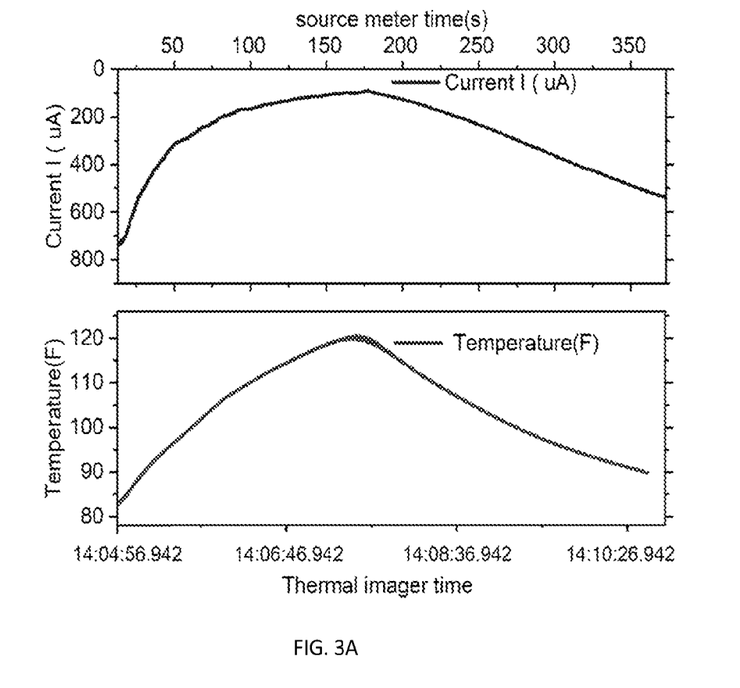
FIGS. 3A and 3B: 3A, change in current through 40 wt % G-ECOFLEX® temperature sensor due to heating and cooling with respect to time. Current was measured by the source measure unit and temperature of the sensor was measured by a thermal imager in the same time frame and plotted separately, top and bottom panel respectively; 3B, an example thermal image of 40 wt % G-ECOFLEX® sensor recorded during the experiment. Heat from a heat gun flows to the sample from the right side in the image and causes brighter contrast in that area.
Figure 3B:
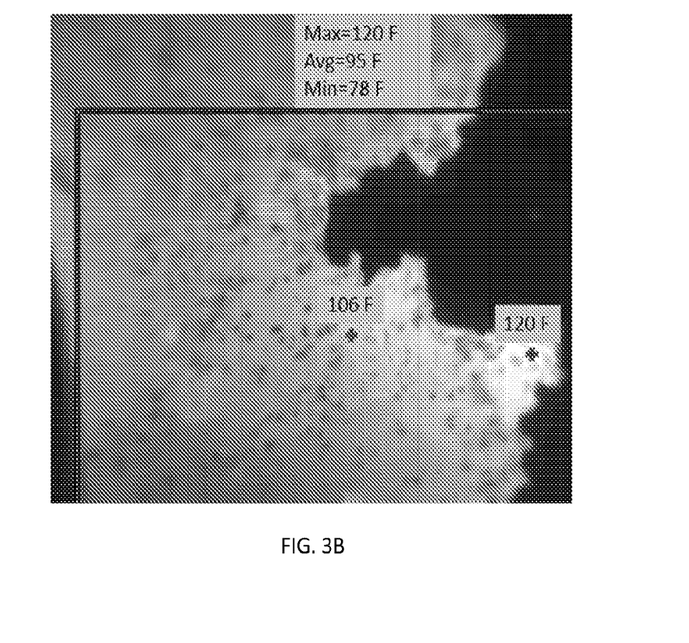

A similar test was performed to determine temperature sensing performance. However, in this case external input in the form of heat was applied by a heat gun pointed to the middle right section of the sensor. Temperature increase in the sensor was detected by a high-resolution thermal imager (RSE 600). FIG. 3A shows that during the test, temperature increase in the sensor as measured by the thermal imager matches well with the change in electrical current through the sensor as measured by the source measure unit, indicating good potential utility of G-EMCs for temperature sensing. There is slight non-linearity at high temperature, which can be analyzed, modeled and addressed in the output algorithm. A sample thermal image from thermal video recorded during the test is presented in FIG. 3B.

Figure 4:
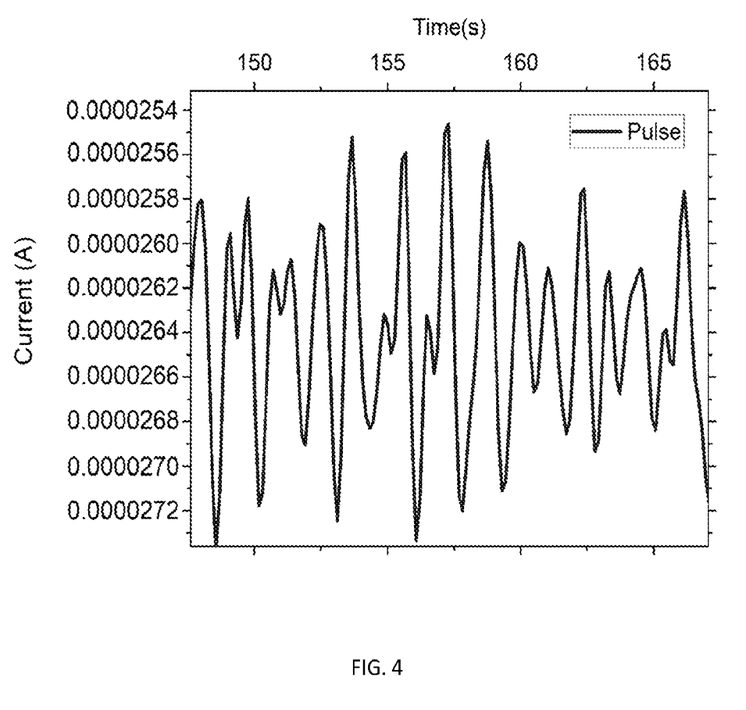
FIG. 4: Pulse detection of G-EMC sensor shown by corresponding electrical current change through the sensor due to blood pressure in the artery.

FIG. 4 shows the pulse detection of a G-EMC sensor of the invention indicated by corresponding electrical current change through the sensor due to blood pressure in the artery. Attachment of G-EMC sensor can be made, for example, to the wrist of a human subject.

Example 2: Graphene- and Hexagonal Boron Nitride (HBN)-Enhanced Silicone

Figure 5A:
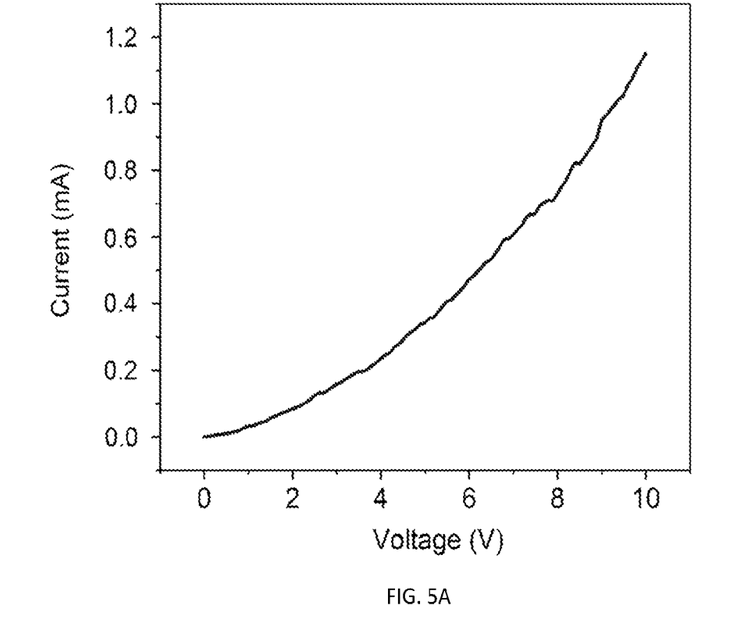
FIGS. 5A and 5B: 5A, current vs. voltage plot of the sample (about 75 mm in diameter and 3 mm thickness) showing good conductivity over large area; 5B, change in current value through the sensor due to finger motions (opening and closing of fist).
Figure 5B:
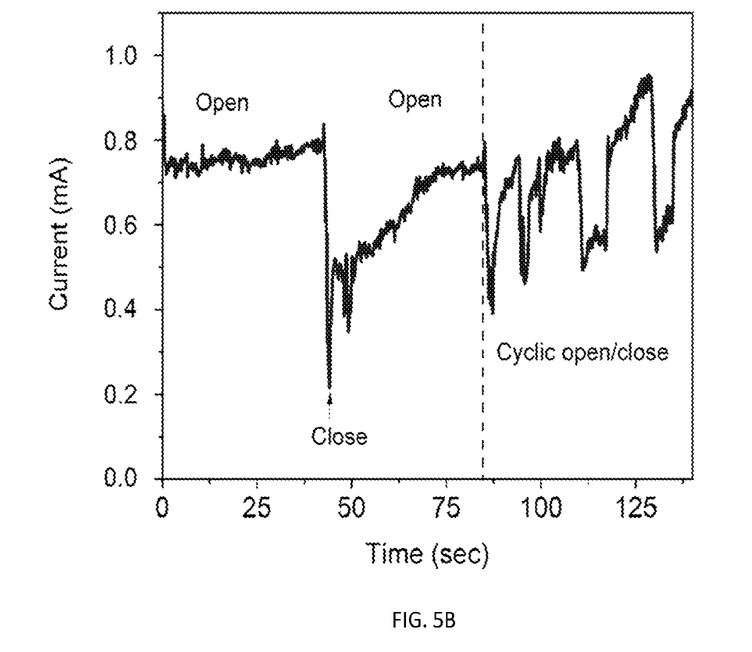

Using shear exfoliation in a melt-processing batch mixing machine, graphite was converted to GNFs and HBN was converted to HBN nanoflakes (HBN-NFs). 35-40 wt % graphite was converted into graphene nanoflakes (GNFs), and 10 wt % bulk layered hexagonal boron nitride (HBN) was converted into HBN nanoflakes directly within a silicone polymer precursor (ECOFLEX®Part A) and the graphite was converted into GNFs and 10 wt % bulk layered hexagonal boron nitride (HBN) was converted into HBN-NFs directly within the curing agent (ECOFLEX®) component by mixing each sample in a batch mixer for 30-40 minutes at 40° C. temperature. The filled polymer precursor was then combined and mixed with the filled curing agent component and allowed to cure, according to the manufacturer's curing conditions but with a different mixing ratio (4 parts polymer precursor to 1 part of curing agent by weight) resulting in highly bendable sensor material. Prepared sample allows significant current flow over large area with applied voltage of ca. 10 V (FIG. 5A), and can be used for different sensing applications like tracking joint or finger movement (FIG. 5B). Change in electrical current through the sensor was detected by a source measure unit (Keithley 2450). Applied voltage never exceeded 10 V, and therefore the power requirement is low for this class of sensors. Small artefacts in the signal coming from external noise can be eliminated by 1) hardware modification to minimize noise, and 2) appropriate mathematical interpolation and filtering algorithms.

The technical aspect of the present methodology that differentiates it from existing technology lies in a layered material which is capable of being exfoliated into conductive 2D nanoparticles (e.g., graphite, molybdenum disulfide, tungsten disulfide, hexagonal boron nitride) being converted to conductive 2D nanoparticles directly within the elastomer precursor and/or curing agent precursor, rather than having to first separate the nanoparticles/nanoflakes from the layered material followed by incorporating the nanoparticles into each phase. In contradistinction to the present state of the art, the present method avoids first creating nanoparticles and then functionalizing the nanoparticles, both of which are costly processes, as well as avoiding handling nanoparticles during composite preparation. Further, the present method achieves superior planar adhesion and primary edge covalent bonding between newly created 2D nanoparticles and the matrix. Additionally, since the raw materials are layered materials rather than 2D nanoparticles, the presently disclosed sensor material is less expensive to produce, and high 2D particle concentration is easily attained. These G-EMC sensors are easily tunable in order to attain the desired property.

For example, graphite is exfoliated into GNFs directly within elastomer precursor and/or curing agent, providing the opportunity for very strong nanoparticle-elastomer interaction and nanoparticle-curing agent interaction, since each new GNF is a pristine surface and fracturing across the AB (basal) plane provides the opportunity for primary covalent bonding to occur between GNF edges and elastomer precursor and/or curing agent. The GNFs can have a distribution in the number of graphene layers and can be controlled by the mixing time, in order to optimize resulting properties of the GNF-Elastomer. Further, the present methodology allows the attainment of high GNF concentration (35-40 wt % GNFs), since the raw material is graphite which is converted to GNFs directly within the elastomer precursors during processing.

In contrast, the present method comprises first, exfoliating graphite to graphene in elastomer precursor, and separately exfoliating graphite to graphene in curing agent in a batch mixer for 30 min at room temperature, and second, mixing graphene-polymer precursor and graphene-curing agent mixtures in a 4:1 to 6:1 ratio, or other suitable ratio based on the elastomer type and graphene concentration, and placing the product under vacuum for 4-6 hours to fully cure. Further, the present method can exfoliate graphite within the elastomer precursor, or the curing agent, or both, allowing exquisitely fine tunability/optimization for a selected property.

Thus, the following differences/benefits versus the state of the art are evident in the presently disclosed method:
1. Separate in situ exfoliation of graphite in polymer precursor and/or curing agent. No need to prepare graphene separately and then blend with a polymer.
2. Less chance of contamination from solvent, more environmentally friendly and less hazardous. No additional cost for solvents that are added, then removed.
3. No need for membrane filtration.
4. Less time consuming, e.g. 5-7 hours for the present methodology versus about 97 hours for art-standard methods.
5. Less expensive due to fewer total process steps (2-3 steps versus 8-10 steps), as well as saving the cost associated with exfoliating the layered material (e.g., graphite) separately.
6. The present methodology is not limited to putty matrices. It can be used with many other elastomers including ECOFLEX® and dragon skin, among others.
7. The present method can accommodate a higher concentration of graphene and is not limited by separate liquid exfoliation throughput to produce graphene.
8. Since there is no exposure of graphene flakes to air in the present method, the graphene particles do not become oxidized. This is a known problem with the sonication technique.

With regard to the other mechanical graphite exfoliation techniques described above:
1. These other mechanical graphite exfoliation techniques differ from the present methodology because they require solvent/surfactant and/or other stabilizers/acid/exfoliating agents, such as melamine/dry ice.
2. These other mechanical graphite exfoliation techniques require longer processing times versus the present methodology. For example, ball milling can require ca. 30 hours.
3. These other mechanical graphite exfoliation techniques are susceptible to contamination and oxidation due to air exposure.
4. The supercritical fluid methodology requires sophisticated handling, special reactors and other specialized equipment.
5. In contrast, the present methodology does not require pre-functionalization of graphene, whereas some of the other methods require pre-treatment of the graphene prior to exfoliation.

In summary, the present method creates enhanced elastomers for the fabrication of flexible wearable sensors for various types of applications. The advantages of the technology derive from the method of making the elastomer/nanocomposite. Layered materials which are capable of being exfoliated are converted to conductive 2D nanoparticles directly within the elastomer polymer precursor and/or curing agent precursor, rather than having to first separate the nanoparticles from the layered material and then incorporate the nanoparticles into each phase. Superior planar adhesion and primary edge covalent bonding between newly created 2D nanoparticles and the matrix is observed.

Alternatively, depending on the elastomer, bonding need not be covalent between the 2D nanoparticles and the matrix, but can also be physical bonding, such as adhesion.

Additionally, since the raw materials are layered materials rather than 2D nanoparticles, this sensor material is less expensive to produce and high 2D concentration is easily attained. These G-EMC sensors are easily tunable in order to attain the desired property. The layered material, which can be of various types, is combined with each of the elastomer precursor and the curing agent separately and exfoliated to provide 2D nanoparticles. For example, a sensor for conductivity can be prepare from Component A: layered material exfoliated (such as graphite turned into graphene nanoparticles) in the polymer precursor, and Component B: layered material exfoliated in the curing agent, by combining Components A and B at different ratios and under conditions to develop a film, where at least one of the layered materials from Components A and B is capable of being exfoliated into conduct 2D nanoparticles. The resulting elastomer nanocomposite containing conductive 2D nanoparticles provides improved mechanical, electrical and thermal properties.

What is claimed is:

1. A method of preparing an elastomer filled with conductive 2D nanoparticles, or a combination of 2D nanoparticles that enhances conductivity, said method comprising:
   a) providing an elastomer polymer precursor, a corresponding elastomer polymer curing agent and one or more layered materials;
   b) (i) blending the elastomer polymer precursor and at least one layered material which is capable of being exfoliated into conductive 2D nanoparticles under shear sufficient to exfoliate the layered material in the elastomer polymer precursor until conductive 2D nanoparticles are formed, to provide conductive 2D nanoparticle-filled polymer precursor, and/or     (ii) blending the elastomer polymer curing agent and at least one layered material which is capable of being exfoliated into conductive 2D nanoparticles, under shear sufficient to exfoliate the layered material in the elastomer polymer curing agent until conductive 2D nanoparticles are formed, to provide conductive 2D nanoparticle-filled curing agent; and c) mixing under curing conditions to form an elastomer:
    i) the conductive 2D nanoparticle-filled polymer precursor and the elastomer polymer curing agent, or
    ii) the elastomer polymer precursor and the conductive 2D nanoparticle-filled curing agent, or
    iii) the 2D nanoparticle-filled polymer precursor and the 2D nanoparticle-filled curing agent, wherein at least one of the 2D nanoparticle fillings is conductive.

2. The method of claim 1, wherein conductive 2D nanoparticle-filled polymer precursor and elastomer polymer curing agent are mixed in step c) to form an elastomer.

3. The method of claim 1, wherein elastomer polymer precursor and conductive 2D nanoparticle-filled curing agent are mixed in step c) to form an elastomer.

4. The method of claim 1, wherein at least one of the 2D nanoparticle-filled polymer precursor and 2D nanoparticle-filled curing agent comprise conductive 2D nanoparticles, and are mixed in step c) to form an elastomer.

5. The method of claim 1, wherein the layered material is selected from the group consisting of graphite, hexagonal boron nitride (HBN), molybdenum disulfide ($MoS_2$), tungsten disulfide ($WS_2$), $MoSe_2$, $MoTe_2$, $WSe_2$, $TaSe_2$, $NbSe_2$, $NiTe_2$, $MoCl_2$, $PbI_2$, $MgBr_2$, $MnO_2$, $MoO_3$, $LaNb_2O_7$, $Mg_6Al_2(OH)_{16}$, GaSe, $Bi_2Te_3$, $Sb_2Se_3$, $TiSe_2$, $VS_2$, $NbS_2$, $TaS_2$, $VSe_2$, $NbSe_2$, $TaSe_2$, $VTe_2$, $NbTe_2$, $TaTe_2$, $PdTe_2$, $PtTe_2$, montmorillonite (MMT), mica, vermiculite, talc, kaolinite, borophene, phosphorene and mixtures of two or more thereof.

6. The method of claim 5, wherein the layered material is graphite or a mixture of graphite and one or more other layered materials.

7. The method of claim 1, wherein the elastomeric polymer comprises a precursor selected from the group consisting of polybutadienes, butadiene copolymers, acrylonitrile copolymers, natural rubber, synthetic rubber, polyester-amides, chloroprene rubbers, poly(styrene-butadiene) copolymers, polysiloxanes, polyisoprene, polyurethanes, polychloroprenes, chlorinated polyethylenes, polyethylene glycols, polyester/ether urethanes, polyethylene, propylene, chlorosulphanated polyethylenes, polyalkylene oxides, polyethylene oxides, fluorosilicones, highly saturated nitriles, nitriles, polyacrylates, silicones, fluorinated ethylene propylene (FEP), perfluoroelastomers, copolymers of tetrafluoroethylene/propylene, carboxylated nitriles, fluoroelastomers, and mixtures thereof.

8. The method of claim 1, wherein the curing agent is selected based on compatibility with the elastomeric precursor and the desired end use application.

9. The method of claim 1, wherein said blending under shear is provided by a batch mixer.

10. The method of claim 1, further comprising the step of curing the polymer product under vacuum, or under ambient conditions, or by applying heat, depending on the type of elastomer.

11. The method of claim 10, wherein the curing time under vacuum is from about 0.1 to about 10 hours.

12. A method of fabricating a sensor, comprising coating, attaching or inserting an elastomer filled with 2D nanoparticles prepared by the method of claim 1 to a suitable substrate.

13. A method of fabricating a sensor, comprising molding or casting an elastomer filled with 2D nanoparticles prepared by the method of claim 1.

14. The method of claim 12, further comprising the step of attaching electrical leads, electrical connectors, or electrodes thereto.

15. The method of claim 12, wherein said substrate is selected from the group consisting of fabrics, rubbers, plastics, metal, wood, electronic components, gloves, wrist bands, shoe soles, and belts.

16. A method of fabricating a sensor, comprising forming an elastomer filled with 2D nanoparticles by the method of claim 1, forming said elastomer into an appropriate shape, and curing.

17. The method of claim 16, further comprising the step of attaching electrical leads, electrical connectors, or electrodes thereto.

18. The method of claim 1, comprising a suitable polymer precursor:curing agent ratio depending on the polymer precursor and curing agent.

19. The method of claim 18, wherein said polymer precursor:curing agent ratio is about 4:1 to about 6:1.

* * * * *